US009653980B2

(12) United States Patent
Laurent

(10) Patent No.: US 9,653,980 B2
(45) Date of Patent: May 16, 2017

(54) ENERGY HARVESTING SYSTEM USING SEVERAL ENERGY SOURCES

(71) Applicant: Universite de Liege, Angleur (BE)

(72) Inventor: Philippe Laurent, Fleron (BE)

(73) Assignee: UNIVERSITE DE LIEGE, Angleur (BE)

( * ) Notice: Subject to any disclaimer, the term of this patent is extended or adjusted under 35 U.S.C. 154(b) by 660 days.

(21) Appl. No.: 14/013,254

(22) Filed: Aug. 29, 2013

(65) Prior Publication Data
US 2013/0342032 A1 Dec. 26, 2013

(51) Int. Cl.
H02K 35/00 (2006.01)
H02K 35/06 (2006.01)
H02K 35/02 (2006.01)
H02K 35/04 (2006.01)
H02K 7/00 (2006.01)
H02N 11/00 (2006.01)

(52) U.S. Cl.
CPC .......... H02K 35/06 (2013.01); H02K 7/00 (2013.01); H02K 35/00 (2013.01); H02K 35/02 (2013.01); H02K 35/04 (2013.01); H02N 11/002 (2013.01); *A61M 2205/8293* (2013.01)

(58) Field of Classification Search
CPC ......... H02K 35/00; H02K 35/02; H02K 35/06
See application file for complete search history.

(56) References Cited

U.S. PATENT DOCUMENTS

| 3,024,374 | A | * | 3/1962 | Stauder | H02K 35/02 310/14 |
| 4,542,311 | A | * | 9/1985 | Newman | H02K 33/16 310/13 |
| 6,700,229 | B2 | * | 3/2004 | Sadarangani | F02B 1/12 310/12.12 |

(Continued)

FOREIGN PATENT DOCUMENTS

| DE | 29511420 U1 | 11/1995 |
| DE | 19852470 A1 | 5/2000 |

(Continued)

OTHER PUBLICATIONS

Shadrach Joseph Roundy, "Energy Scavenging for Wireless Sensor Nodes with a Focus on Vibration to Electricity Conversion", the university of California, Berkeley, pp. 11-13, 2003.

*Primary Examiner* — Dang Le
(74) *Attorney, Agent, or Firm* — Jacobson Holman, PLLC.

(57) ABSTRACT

An object of the invention is to provide a cheap, efficient and polyvalent energy harvesting system able to exploit several energy sources. The invention proposes an energy harvesting system (100) including a frame, at least one permanent magnet (101) having a North/South direction, and at least one winding (107, 108) wound according to a winding direction around a core (103a-103b) including a high magnetic permeability material, at least said at least one permanent magnet being mounted on the frame to be able to oscillate relatively to the winding, characterized in that the system includes a magnetic flux divider arranged between said at least one permanent magnet and said at least one winding in order to concentrate the magnetic flux at discrete positions of maximum magnetic flux then forming equilibrium positions where the winding faces one of the said discrete positions of maximum magnetic flux.

21 Claims, 9 Drawing Sheets

(56) References Cited

U.S. PATENT DOCUMENTS

| | | | |
|---|---|---|---|
| 6,748,907 B2 * | 6/2004 | Malmquist | B60K 6/46 123/46 E |
| 2003/0034697 A1 * | 2/2003 | Goldner | B60G 17/0157 310/17 |
| 2005/0218728 A1 * | 10/2005 | Stewart | F03B 13/1845 310/12.12 |
| 2007/0135756 A1 | 6/2007 | Kohlbrenner et al. | |
| 2010/0327672 A1 * | 12/2010 | Roberts | H02K 35/00 310/25 |
| 2011/0109173 A1 * | 5/2011 | Sugita | H02K 33/16 310/12.18 |
| 2011/0142522 A1 | 6/2011 | Yeh | |
| 2011/0285487 A1 | 11/2011 | Schmidt | |

FOREIGN PATENT DOCUMENTS

| | | |
|---|---|---|
| DE | 102005059508 A1 | 6/2007 |
| DE | 102007052784 A1 | 5/2009 |
| WO | 03/075441 A2 | 9/2003 |
| WO | 2004/093299 A1 | 10/2004 |
| WO | 2007/038157 A2 | 4/2007 |

* cited by examiner

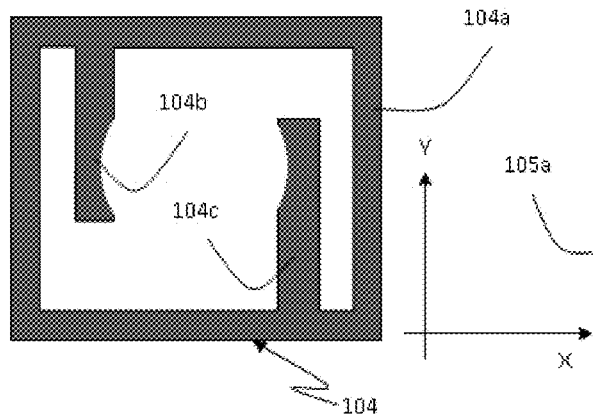
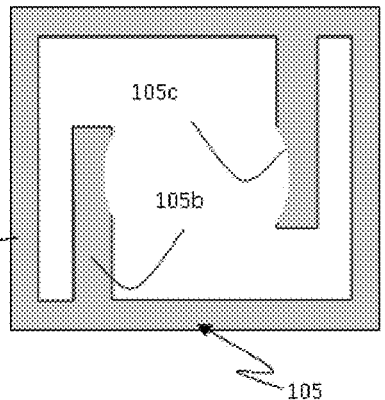
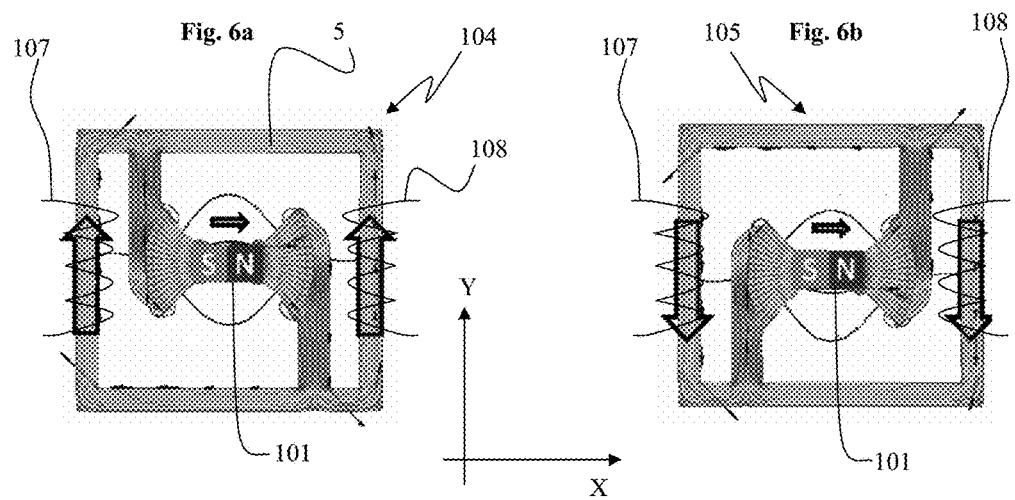

Δz2

Δz4

ENERGY HARVESTING SYSTEM USING SEVERAL ENERGY SOURCES

The invention relates to an energy harvesting system using several energy sources.

Nowadays, electronics need small amounts of energy to work. For that reason, microsystems can be powered by energy harvested from the environment. For example, energy can be scavenged from ligth (photovoltaic technology), from heat flux (thermogenerators), or from vibrations.

As explained by S. J. Roundy, if the microsystem has to be powered for a long period, the energy harvesting is a good solution compared to the battery technology ["Energy Scavenging for Wireless Sensor Nodes with a Focus on Vibration to Electricity Conversion", Shadrach Joseph Roundy, 2003].

A first drawback of a known energy harvesting system is that it can produce energy only when the energy source is active. However, the presence of the energy source is uncertain.

A second drawback of energy harvester is the low efficiency of the energy conversion.

Many type of energy harvesting system are known, each adapted to harvest one type of energy.

For example, a known energy harvesting system is described in document WO 2007/038157. It is a vibration-based energy harvesting system. It consists in a cantilever beam made of piezoelectric material electrically connected to a harvesting circuit. This system can convert mechanical energy to electrical energy by submitting the beam of piezoelectric material to vibration.

This type of energy harvesting system can only convert vibration in electrical energy. That means that it is not useful if there is no vibration. Another type of energy harvesting system has to be used.

An object of the present invention is to provide a cheap, efficient and polyvalent energy harvesting system able to exploit several energy sources.

The invention, fully detailed in this description, can exploit up to six different energy sources:
  a. Dynamic motions:
    mechanical vibrations
    impacts
    shock absorber
  b. Slow motions:
    moving parts
    human breathing
    walking
    variable mass
    liquid level variation
    slow motions created by a slow pressure drift
  c. Rotation:
    motor (high speed)
    wheel
    wind turbine
  d. Small swing:
    pendulum
    elbow
    knee
  e. Slow temperature variation:
    air day/night
    air sunny/cloudy
    running heat engine or not
    running electrical engine or not
    lake temperature winter/summer
    air surrounding a plane wing ground/sky
  f. Heat flux:
    black surface exposed to sunrays/air cooled surface
    heat engine casing/air or water cooled surface
    electrical engine casing/air or water cooled surface
    fire/cooled surface
    hot water/ambient air or cold water The accompanying drawings, which are included to provide a further understanding of the invention and to illustrate embodiments of the invention together with the description, serve to explain the principle of the invention. In the drawings:

FIGS. 5a and 5b are plan views illustrating a first shape of magnetic plates intended to be stacked to form a magnetic circuit;

FIGS. 6a and 6b are schematic views illustrating the magnetic fields flowing through the magnetic plates of FIGS. 5a and 5b;

The energy harvesting system according to the invention comprises a frame 1b, at least one permanent magnet 7 having a North/South direction, and at least one winding 6 wound according to a winding direction around a core 5 comprising a high magnetic permeability material, at least the permanent magnet 7 being mounted on the frame 1b to be able to oscillate relatively to the winding 6, characterized in that the system comprises a magnetic flux divider arranged between said at least one permanent magnet and said at least one winding in order to concentrate the magnetic flux at discrete positions of maximum magnetic flux, separated by minimum magnetic flux position, then forming equilibrium position when the winding faces one of the said discrete positions of maximum magnetic flux.

According to a first embodiment, the magnetic flux divider may be constituted by a stack of a plurality of permanent magnets separated from each other by a fixed spacing (the distance between two adjacent magnets defines a "step"), the polarizations North/South of two consecutive magnet being alternated.

The spacing is constituted by a non conductive and non magnetic material such as air, a polymer, ceramic, paper, fabric, and the like to electrically and magnetically insulate the magnets from each other.

According to a second embodiment, the magnetic flux divider may comprise at least two magnetic guides made of a material having high magnetic permeability, separated by a magnetic and electric isolator made of non conductive material, the magnetic guides being arranged between said at least one permanent magnet and said at least one winding.

The magnetic flux divider concentrates the magnetic flux at discrete positions of maximum magnetic flux. The maximum magnetic flux positions are thus separated from each other by minimum magnetic flux position.

Figure 1:
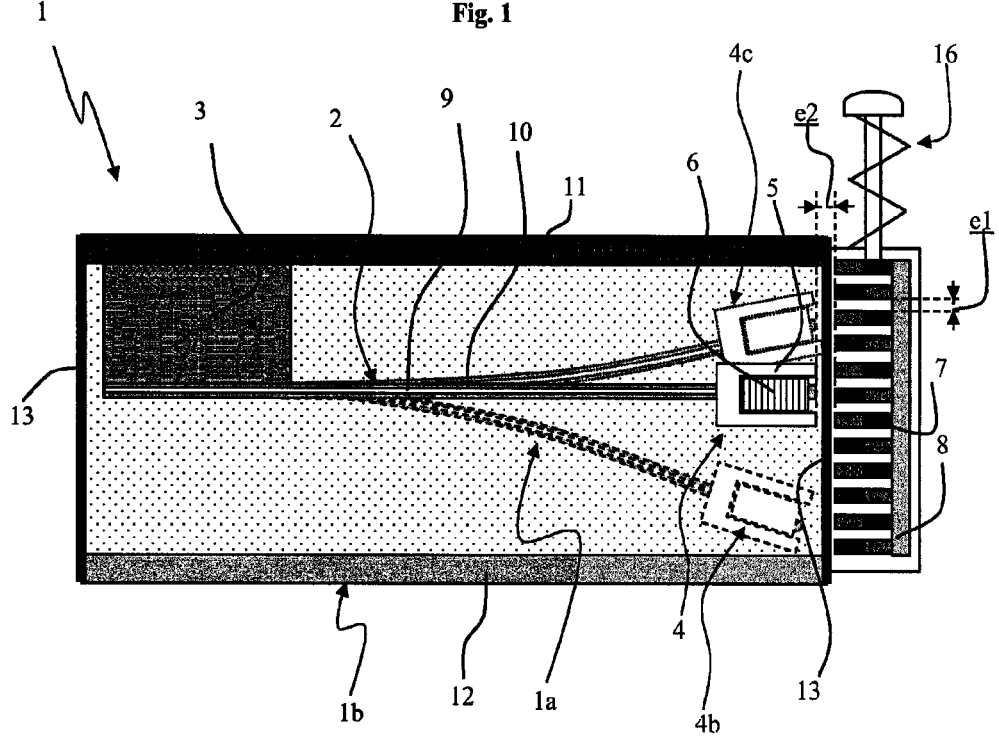
FIG. 1 is a sectional view illustrating a first embodiment of an energy harvesting system according to the invention
Figure 2:
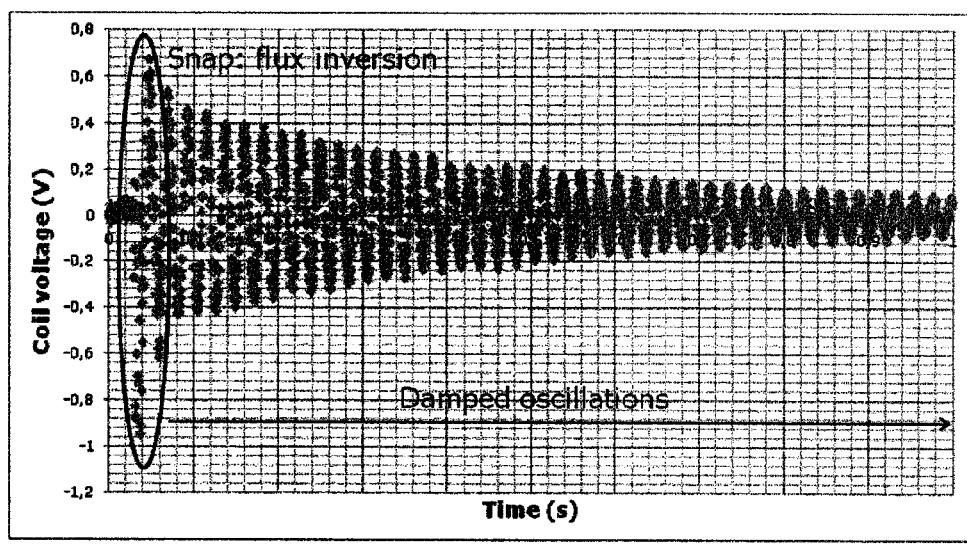
FIG. 2 is a graph depicting the voltage obtained with an energy harvesting system according to the invention, in function of time.

Thus, that structure defines equilibrium position all along the run, when the winding faces one of the said discrete positions of maximum magnetic flux The first embodiment of an energy harvesting system 1 according to the invention is described in relation with FIGS. 1 and 2. This embodiment is able to harvest energy in four operating modes (modes a, b, e and f cited here above).

It comprises an energy converter 1a transforming raw energy taken from the environment into energy that can be used to power a microsystem (electrical energy), and a frame 1b.

Generally speaking, the energy converter 1a is based on:
A system able to store and release energy. Using such a system, the energy conversion is made step by step, leading to a high efficiency,
Magnetic flux inversion.

More precisely, the first embodiment 1 of the energy harvesting system according to the invention comprises an energy converter 1a comprising a cantilever beam 2 with an extremity clamped to the frame 1b via a clumping 3 and a free extremity, the beam having a beam core 9 made of a material allowing an oscillating movement of the free extremity. A high frequency (HF) mass 5-6 is mounted at the free extremity of the cantilever beam 2, the high frequency mass 5-6 being formed by the winding 6 wound around a mass core 5 comprising a high magnetic permeability material.

In the described system, the beam plays the role of a spring to store mechanical energy transmitted by the environment.

The windings 6 consist in a number of turn made of insulated copper wire, wound around a mass core 5. The mass core 5 is made in a material with a high magnetic permeability (e.g. iron). The mass core 5 may be 'I' shaped, 'U' shaped, 'E' shaped or other. It is fixed at the free end of the beam.

The windings generate electromotive force when subjected to a variation of the magnetic flux. The mass core 5 decreases the magnetic reluctance and increases the magnetic flux. With its shape, it concentrates de magnetic flux and, thus, defines equilibrium positions for the HF mass 5-6.

At least two permanent magnets 7 are fixed and arranged to a magnet support 8 made of high magnetic permeability material, such that
the North/South direction of each magnet 7 is perpendicular to the magnet support 8,
the permanent magnets 7 are separated from each other by a fixed spacing e1, (the distance e1 between two adjacent magnets defines a "step")
that magnet polarizations are alternated, it means that if a permanent magnet 7 is fixed to the magnet support 8 by its North pole, the adjacent permanent magnet is fixed to the magnet support 8 by its South pole.

The permanent magnets 7 and the magnet support 8 form a magnetic track 7-8.

The magnet support 8 is a bar made of a material with a high magnetic permeability (e.g. iron). The magnet support 8 decreases the magnetic reluctance, and increases the magnetic flux.

The spacing e1 may be constituted by non conductive and non magnetic material such as air, a polymer, ceramic, paper, fabric, and the like. to electrically and magnetically insulate the magnets 7 from each other.

The structure of magnets alternating with non conductive and non magneticmaterial (such as air, a polymer, or other non conductive material[1]) concentrates the magnetic flux in direction of the HF mass 5.

Thus, that structure defines several equilibrium positions between the magnets 7 and the HF mass 5 all along the run.

This enhances the efficiency of the harvesting system because the mass-spring system is allowed to work at a frequency largely different of its natural frequency. The system is then fully capable to produce electrical energy with a high efficiency for very low frequencies—even in a quasi-static mode.

The current research tendencies in the field aim at increasing the bandwidth by using non linear springs for example, or multiplying the mass-spring systems. However, in the described system according to the invention, as the energy is stored most of the time, the natural frequency matching is not a problem anymore. When the energy is suddenly released during the pulse, the mass system systematically works at its natural frequency, where it has been designed to be the most efficient.

This is made possible because several equilibrium positions exist due to the magnetic flux divider. Then, energy can be stored between two equilibrium positions.

In order to improve the efficiency, the first embodiment illustrated in FIG. 1 comprises a HF mass shaped in "E", the winding being wounded around the middle arm of the "E".

Equilibrium positions are obtained when the external arms of the "E" face two magnets. When the external arms of the "E" are located between two magnets, it is not an equilibrium position. Therefore, the mass core tends to reach the next equilibrium position, thus enhancing the efficiency of the energy harvesting system according to the invention.

In a rest position (position 4), the winding faces one permanent magnet 7 such that the winding direction is parallel to the North/South direction and such that the winding is separated from the permanent magnets by a fixed spacing e2.

In the illustrated example, the magnet support is also elastically mounted relatively to the frame 1b. The magnet support is mounted in a push button 16 having a part attached to a compression spring. In the described system, the push button allows a relative displacement between the permanent magnets 7 and the HF mass 5-6.

The beam core 9 is made of a spring material such as steel to harvest mechanical energy.

Advantageously, the beam core 9 may be made of a material chosen from a shape-memory alloy and a bimetallic assembly. Thus, the beam plays the role of a thermoactuator.

A thermoactuator is a thermo-mechanic device which can perform a gradual stroke, even with a load. It contains a heat sensitive substance/structure which expands when subjected to a temperature change.

It is therefore possible to generate electricity from temperature change by deforming the beam, which then oscillates in front of the permanent magnets 7 when switching from one equilibrium position to another.

To this end, the frame of the energy harvesting system is a housing comprising a hot panel 11 parallel to a cold panel 12, and adiabatic panels 13 bindings the hot panel 11 ant the cold panel 12 to form a cavity of the housing where the energy converter 1a is located between the hot panel 11 ant the cold panel 12.

The hot panel 11 consists in a plate made in thermally conductive material (e.g. aluminum). Its top surface could be matt black. The hot panel plays the role of a hot reservoir (thermal mass). Note that the hot panel, in some operating modes, is not necessarily hot.

The beam is clamped to the hot panel 1 by a metallic block 3. The metallic block consists in block made in copper for example. It allows a thermal link between the thermoactuator (beam) and the hot panel 11.

The cold panel 12 consists in a plate made in thermally conductive material (e.g. aluminum). The cold plate plays the role of a cold reservoir (thermal mass). Note that the cold plate, in some operating modes, is not necessarily cold.

To be colder than the hot panel 11, le cold panel 12 may be in contact with a cold source, or may be equipped with a heat sink.

The adiabatic panels 13 consist in walls made in a low conductive material (e.g. thermoplastic). The adiabatic panels play the role of thermal insulation between the hot panel and the cold panel.

Optionally, the air of the cavity may be removed to form a vacuum cavity. It helps to decrease mechanical losses due to friction and to decrease heat flux leakage between the hot and the cold panel.

The locations of the beam when hot (4b: in dashed lines) or cold (4c: in dotted lines) are depicted in FIG. 1, whereas the reference position of the beam (room temperature) is straight (4).

Optionally, the beam further comprises external layer 10 made of piezoelectric material. Thus, when subjected to strains, the external layers generate electricity thanks to the piezoelectric effect. It improves energy harvested during the oscillation of the beam.

The common point of the four working modes a, b, e, f is the conversion of energy into a high speed displacement between magnets and a coil, bringing to a magnetic flux variation. This flux variation is picked-up by the coil and a voltage appears at the end of the windings due to Faraday's law. In parallel, if piezoelectric layers are used, a voltage is produced by the strain of piezoelectric layer. The voltage can be rectified and stored in capacitors or batteries for example. Electrical energy is then used to power a microsystem.

When a relative displacement between the HF mass 5-6 and the permanent magnets 7 occurs, electrical energy is produced step by step, that means each time the relative displacement is equal or superior to distance e1.

The way to produce that relative displacement is explained hereafter, together with the mechanisms of the energy conversion:

The HF mass 5-6 is located in an equilibrium position (4). This equilibrium position corresponds to the location where the magnetic reluctance is minimum, i.e. the air gap e2 between the magnetic shape 6 and the magnets 7 is minimum.

As a relative displacement between the HF mass 5-6 and the magnets 7 appears, the magnetic shape 6 is attracted by the magnets 7. So doing, the beam is deflected and energy is stored as an elastic strain. As long as the magnetic force applied on the magnetic shape is higher than the restoring force, energy is stored in the spring (beam).

When the spring force exceeds the magnetic force, the mechanical energy stored is suddenly released and the HF mass snaps from its initials position to the new equilibrium position. As the magnet polarizations are alternated, the magnetic flux picked-up by the windings is inverted during the position switch, leading to a high induced voltage (see FIG. 2). The voltage amplitude increases with the number of turns of the windings, according to Faraday's law.

Due to inertial effect, the HF mass will move following a damped oscillation. The damping is due to (i) mechanical to electrical energy conversion and to (ii) losses. The frequency of the oscillation depends on the HF mass and the global spring constant.

This first embodiment can operates according to mode a, b, e or f.

In the dynamic motions mode a, the mechanical solicitation (vibration random or not, shock) is applied on the housing 1b. The HF mass 5-6 will act as a seismic mass. A relative displacement, between the HF mass 5-6 and the magnetic track 7-8 will occur. Two cases can be differentiated:

The acceleration is lower than a threshold value: the HF mass oscillates around one equilibrium position The acceleration is higher than the threshold value: the HF mass snaps from one equilibrium position to another equilibrium position. In this case, the energy conversion is higher.

In the slow motions mode b, a slow displacement is applied on the push button. So doing, the magnetic track 7-8 will move regarding the HF mass 5-6. The speed of the displacement can be very low while keeping a high efficiency for the energy conversion. In fact, the energy storage through a spring system does not show auto-discharge effect, in opposition with capacitors or batteries.

As long as the displacement is large compared to the step size, many pulses are created during the displacement. The step is defined as the distance between two adjacent magnets. Each pulse corresponds to some electrical energy amount, that can be used by the microsystem directly or at a later time.

In the slow temperature variation mode e, let consider that the temperature of the whole system is increasing by example. The thermoactuator 2 depicted in FIG. 1, will be deformed pushing the HF mass 5-6 to shift downwards. If the deflection is at least larger than the step size e1, a pulse (or more) is created. So doing, a voltage appears at the end of the windings due to Faraday's law.

Note that the temporary energy storage through a spring system offers to the system to work even if the temperature variation is very slow. The conversion of energy stored will be delayed until the snap between two equilibrium positions.

In the heat flux mode e, let consider that the thermoactuator and the hot panel are initially cold. As soon as the hot panel is heated (e.g. sunrays), the thermoactuator, thermally linked to the hot panel through the metallic block 3, starts to be deformed. So doing, the HF mass shifts downwards and pulses are created. The motion continues until the thermoactuator contacts the cold panel. At that time, heat is extracted from the thermoactuator and its temperature decreases. As the thermoactuator is cooling down, the HF mass moves upwards and new pulses are created. The thermoactuator will reach a minimum temperature before to heat again. Then a new cycle start again.

Note that both the period of one cycle and the value of the two extreme temperatures depend on the thermal characteristic time. As the adiabatic panels have a low thermal conductivity, the mean thermal resistance of the whole system is high. Indeed, most of the time, the hot panel is isolated from the cold panel. This point makes the system very attractive compared to thermogenerators.

A preferred realization of an energy harvesting system according to the invention is illustrated in FIGS. 3 to 12*b*. This second embodiment allows reducing the size of the energy harvesting system to obtain a compact device.

Compared to the first embodiment of the system, the compact version brings a lot of advantages:
  Smaller volume
  Higher efficiency
  Allows mode c (rotation) and mode d (swing)
  Reduction of the step size
  Reduction of the air gap
  Can work with only one magnet
  Compensation of the magnetic force acting on the magnet
  The HF mass does not include the windings (brittle)

The compact system 100 (see FIG. 3 and FIG. 4), allowing up to six modes, comprises in a rest position one permanent magnet 101 elastically mounted on a frame 102, whose the allowed motion is perpendicularly to the North/South direction D of the magnet 101. The permanent magnet 101 generates magnetomotive force in the device according to the invention.

A magnetic circuit 103 surrounds the permanent magnet 101 such that is faces both the North and South poles of the permanent magnet. The magnetic circuit 103 comprises magnetic plates 104-105 (respectively in light-gray and dark-gray on the figures; see FIGS. 5*a* to 6*b* for shape examples of the magnetic plates in a plan view) alternatively stacked in a stack direction with plates 106 (in white on the figures) made of non conductive and non magnetic material to electrically and magnetically insulate the magnetic plates 104-105 from each other.

At least one winding 107 is wound around one part 103*a* of the magnetic circuit 103 located in a same side as the North Pole of the permanent magnet 101. At least one winding 108 is wound around one part 103*b* of the magnetic circuit located in a same side as the South Pole of the permanent magnet 101. A second winding superimposed can be used to control circuit (rectifier).

A part 103*c* of the magnetic circuit 103 is located between the part 103*a* equipped with the winding 107 and the permanent magnet 101, and a part 103*d* of the magnetic circuit 103 is located between the part 103*b* equipped with the winding 108 and the permanent magnet 101.

The magnetic circuit plays the role of core of the windings and constitutes a magnetic flux guide and a magnetic flux inverter. The windings generate electromotive force when subjected to a variation of the magnetic flux.

The magnetic circuit 103 is fixed to the frame by support of the magnetic circuit 116.

The frame 102 is a housing comprising a container 109 and a lid 110 elastically mounted on each other via a compression coil spring 111.

The container 109 and the lid 110 are nestable cylinders each having an extremity closed by a flat panel, respectively 109*a* and 110*a*.

The lid 110 plays the role of a push button and a rotating button. The container 109 plays the role of a stop and groove for the compression coil spring 111, and a stop for the push button. The spring 111 forces the push button upwards when unloaded.

The permanent magnet is elastically mounted on the frame by two opposite springs: one 112 fixed to the lid 110, the other 113 fixed to the container 109.

At least one 112 of the springs is preferably a flat spiral spring comprising at least one spiral blade wider than thicker. In another embodiment not shown, the springs supporting the permanent magnet 101 may be coil springs. In that case, the movements of the permanent magnet 101 must be guided in order to forbid a movement along the X axis to avoid that the permanent magnets contacts and collapses with the magnetic circuit 103.

The spring 113 is able to store energy when subjected to a solicitation parallel to the z-axis. The spring constant of the spring 113 in the x and y-direction must be high.

The second embodiment comprises a magnetic flux divider constituted by at least two magnetic guides or "spreaders" made of a material having high magnetic permeability, separated by a magnetic and electric isolator made of non conductive and non magnetic material.

The spreaders concentrate the magnetic flux at discrete positions of maximum magnetic flux. The maximum magnetic flux positions are thus separated from each other by minimum magnetic flux position located in front of the magnetic and electric isolator made of non conductive material.

In the example illustrated in FIGS. 3 to 12*b*, the system comprises, at each pole of the permanent magnet 101, three spreaders 114 made of a material having high magnetic permeability, the spreaders 114 being arranged in order to guide and, thus, concentrate magnetic flux in direction of the magnetic circuit 103. The spreaders 114 are separated by a layer of non conductive and non magnetic material, such as air, a polymer, etc. to electrically and magnetically insulate the spreaders 114 from each other. Thus, the spreaders 114 define several equilibrium positions relative to the magnetic plates 104-105 of the magnetic circuit 103.

The permanent magnet and the spreaders are embedded in a holder 115 fixed to the springs 112-113. The holder 115, the permanent magnet 101 and the spreaders 114 constitute the HF mass (high frequency) of the device.

The holder 115 consists in a polymer block where the magnet and the spreader are embedded. It is anchored to the spring 112 and put in contact with the spring 113. The rotation between the holder 115 and the spring 113 is free. The spring 113 guides the HF mass.

Figure 3:
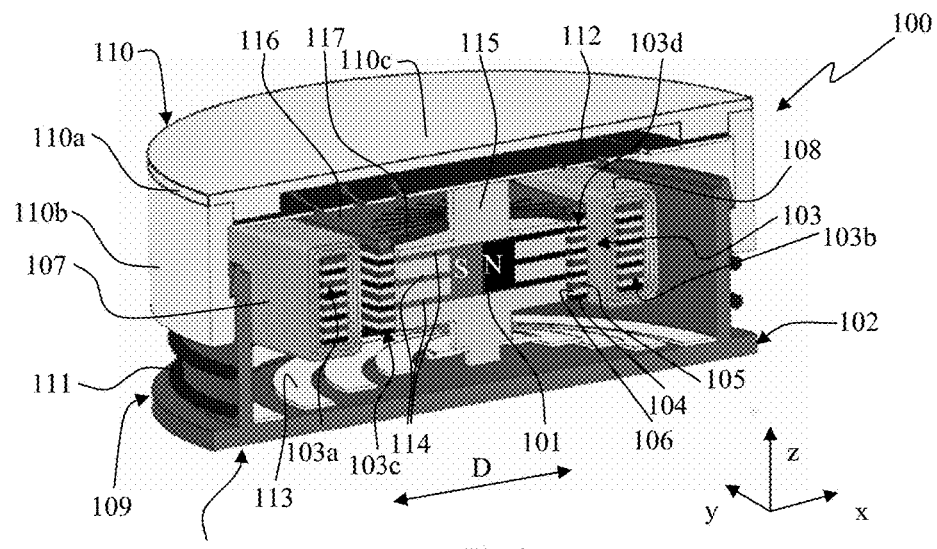
FIG. 3 is a perspective view illustrating a second embodiment of an energy harvesting system according to the invention.
Figure 4:
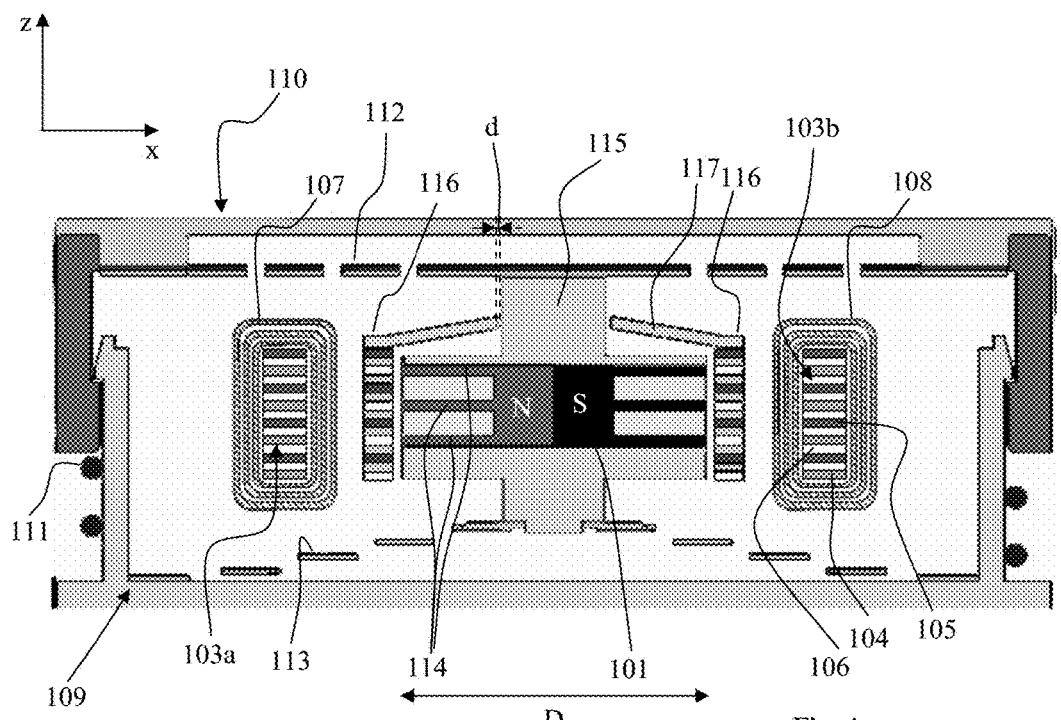
FIG. 4 is a sectional view illustrating the energy harvesting system of FIG. 3.

In an advantageous embodiment of the energy harvesting system according to the invention, one 112 of the springs further comprises a thermoactuor able to move the permanent magnet 101 when the thermoactuor 112 is subjected to a temperature change. The thermoactuator may be realized using bimetallic element, shape memory alloy, a phase transition (e.g. liquid/gaz), or the volume variation of a material (gas, liquid or solid) when subjected to a temperature change. In FIGS. 3 and 4, the thermoactuator is a bimetallic element shaped as a spiral flat spring to further present the function of a spring.

The thermoactuator 112 is anchored to the flat panel 110*a* of the lid 110 which is, in that embodiment, in thermally conductive material (e.g. aluminum). It constitutes the "hot" plate of the device. The outer cylinder 110*b* of the lid 110 is made in a low conductive material (e.g thermoplastic) and fixed on the hot plate. The outer cylinder 110*b* plays the role of a stop and groove for the push button, and of thermal insulation between the hot plate 110*a* and the cold block constituted by the container 109 (see hereafter).

The thermoactuator 112 is also anchored to the holder 115. The external top surface 110c of the flat panel 110a should be matt black. The hot plate 110a is a hot reservoir (thermal mass).

The flat panel 109a of the container 109 constitutes the "cold" plate of the device. It is made of thermally conductive material (e.g. aluminum). The cold plate 109a is a cold reservoir (thermal mass).

The thermoactuator 112 plays the role of:
Actuator, when it is subjected to a temperature change, able to shift the HF mass downward or upward
Energy storage system
A part of the spring-constant for the HF system in translation and rotation
Guidance for the magnet+spreaders. The spring constant of the spring 112 in the x and y-direction must be high
Rotation to translation converter.

In that embodiment, the support of the magnetic circuit 116 is mechanically and thermally anchored to the container 109, which means to the "cold" reservoir.

Figure 12A:
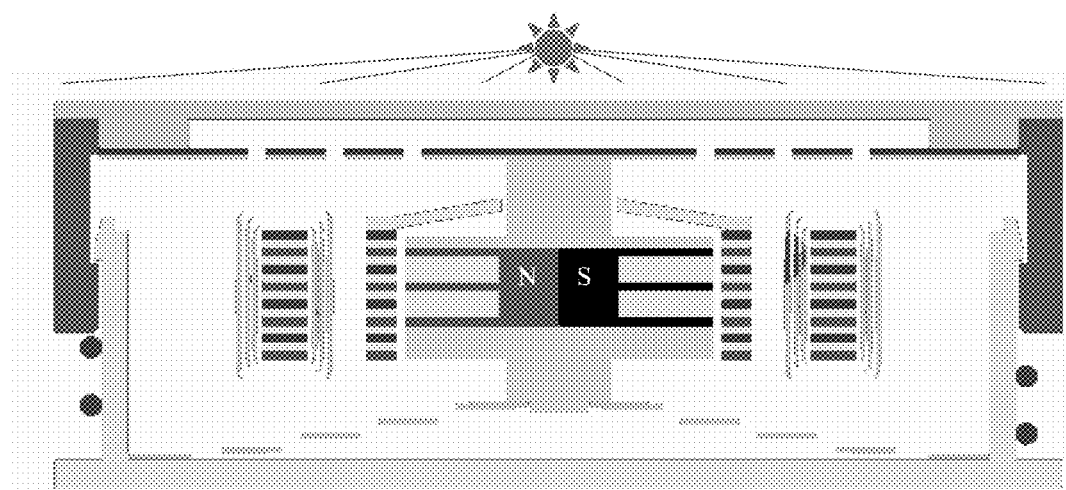
FIGS. 12a and 12b are sectional views illustrating the working of the second of an energy harvesting system according to the invention, for harvesting energy of a heat flux.
Figure 12B:
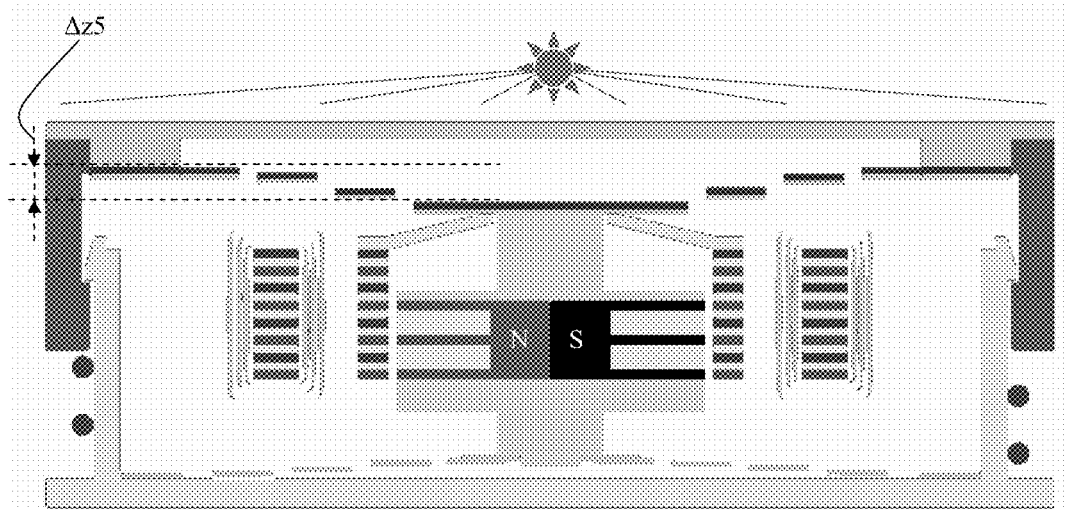

Here, the support of the magnetic circuit 116 further comprises thermally conductive fingers 117 arranged relative to the spring comprising the thermoactuator 112 in order to contact and cool the thermoactuator 112 when it is deformed in response to a given temperature change (see FIGS. 12a-12b). In other words, the cold fingers 117 play the role of a thermal bridge between the thermoactuator and the cold block when touching.

If the distance d between the fingers 117 and the support 115 is sufficiently small, the cold fingers 117 also act as guides along the z axis for the support 115 and thus for the magnet 101 and the spreaders 114.

In that embodiment, the magnetic circuit 103 also plays the role of a large thermal mass (cold).

FIGS. 5a and 5b illustrate two embodiments of magnetic plates 104-105 constituting a part of the magnetic circuit 103.

In general, the magnetic plates have a ring shape part 104a, 105a. Other shapes may be chosen such as, for example rectangular ring shape, an oval ring shape, etc. The magnetic plates further comprise two cantilever arms, respectively 104b-104c, 105b-105c, extending along opposite internal directions of the ring shape. The shape of these cantilever arms can be straight or curved.

To form the magnetic circuit 103, several magnetic plates 104 can be stacked together, each magnetic plates 104 being separated from the one above and the one underneath by a layer of non conductive and non magnetic material.

Alternatively, the stack may be obtained with magnetic plates 105.

When positioned in the energy harvesting system, the cantilever arms 104b-104c, 105b-105c are directly facing the spreaders 114 attached to the poles of the permanent magnet, the ring part 104a, 105a surrounding the cantilever arms and the magnet.

Consecutive magnetic plates may be arranged such that their respective arms are in same positions.

Preferably, consecutive magnetic plates are arranged such that their respective arms are in opposite positions. This allows an inversion of magnetic field when the magnet moves along the z axis from one step to another, as it is shown in FIGS. 6a-6b.

Advantageously, the cantilever arms are symmetrical relative to the center of the ring shape. This is important to obtain the same intensity of magnetic field in each arm. It is also useful for industrialization. Indeed, the magnetic plate 105 is the image in a mirror of the magnetic plate 104. Thus, to obtain inversions of magnetic field, only one type of magnetic plate 104 can be made but, during stacking, consecutive magnetic plates are inversed such that their respective arms are in opposite positions. This solution is very economic and efficient in terms of energy harvesting because of the inversion of magnetic field.

In FIGS. 6a-6b, the results are shown for two different z positions of the magnet+spreaders. In the first z position (FIG. 6a), the magnet and the spreaders are just in front of a magnetic plate of type 104. They are directly facing the cantilever arms 104b and 104c. In the second z position (FIG. 6b), the magnet and the spreaders are just in front of a magnetic plate of type 105. They are directly facing the cantilever arms 105b and 105c.

As depicted on the figures, the magnetic flux direction along the y-axis is inverted in the core of the windings 107-108, each z-position corresponding to an equilibrium position. The magnetic circuit 103 is obtained by stacking of magnetic plates of type 104 and magnetic plate of type 105 in an alternating way. The distance separating two adjacent magnetic plates is called the "step".

If, for some reason, the HF mass (magnet, spreaders and holder) moves along the z-direction, the following phases occur:

The HF mass is strongly held close to its initial position due to the magnetic interaction between the magnetic plates of type 104, for example, and the spreaders. Mechanical energy is stored in the spring HF and the spring/thermoactuator.

The spring force exceeds the magnetic force, the mechanical energy stored is suddenly released and the HF mass snaps from its initials position to the new equilibrium position (spreaders in front of magnetic plates of type 105). As explained, the magnetic flux picked-up by the windings is inverted, leading to a high induced voltage (see FIG. 2)

Due to inertial effect, the HF mass will move following a damped oscillation. The damping is due to (i) mechanical to electrical energy conversion and to (ii) losses. The frequency of the oscillation depends on the HF mass and the global spring constant.

The voltage amplitude increases with the number of turns of the windings 107-108, according to Faraday's law.

The work to decrease the size (or step) is done on the specific frame shapes and arrangement, which directs the flux line through the coils. So doing, the coil size can be kept at a certain level, where it can lead to a high efficiency. Indeed, contrarily to the state of art where the coils have a 2D geometry, the coils designed in the second embodiment system have a 3D geometry, with an iron core, leading to a large inductance value compared to the low inductance for a flat coil (many order of magnitude). Then, a much larger voltage will appear for a given motion, compared to a 2D coil.

As it will be explained, the second embodiment of the energy harvesting system according to the invention offers up to six different operating modes that can be used alone or in combination:
a) Dynamic motions
b) Slow motions
c) Rotation
d) Small swing
e) Slow temperature variation
f) Heat flux Modes a, b, d, e, f are based on a relative displacement, between the HF mass and the magnetic circuit, parallel to the z-axis. Mode c and d are based on a relative rotation, between the HF mass and the magnetic circuit, around the z-axis.

Each operating mode is described hereafter, in relation with FIGS. 7a to 12b where the winding is shown in a partial cut view (the parts above and below the stack of magnetic plats are not shown).

Figure 7A:
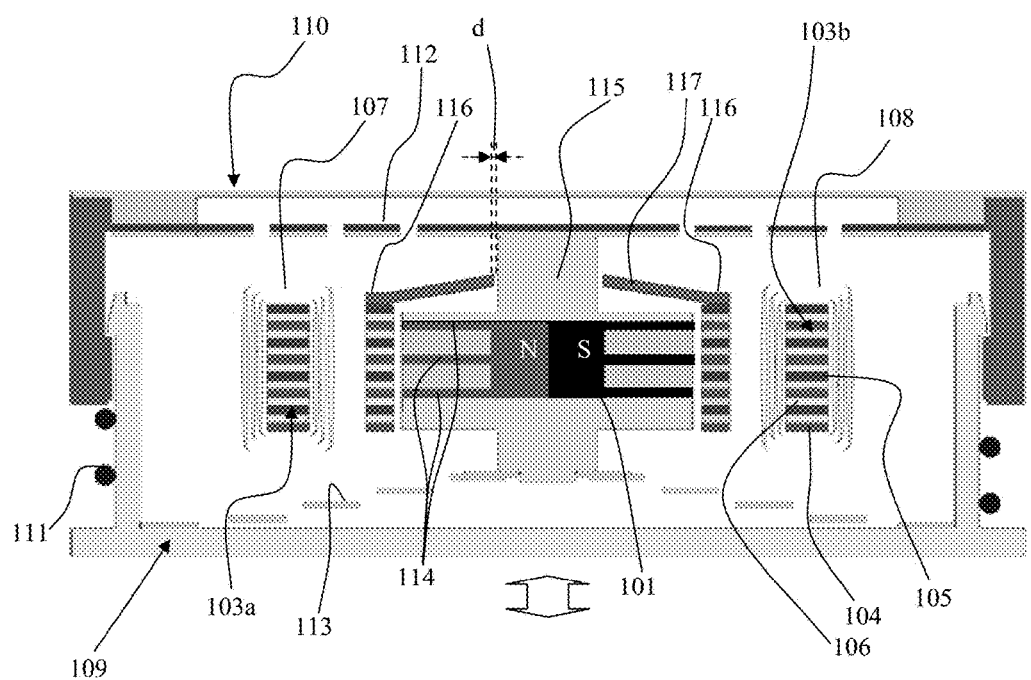
FIGS. 7a and 7b are sectional views illustrating the working of the second of an energy harvesting system according to the invention, for harvesting energy of a dynamic motion.
Figure 7B:
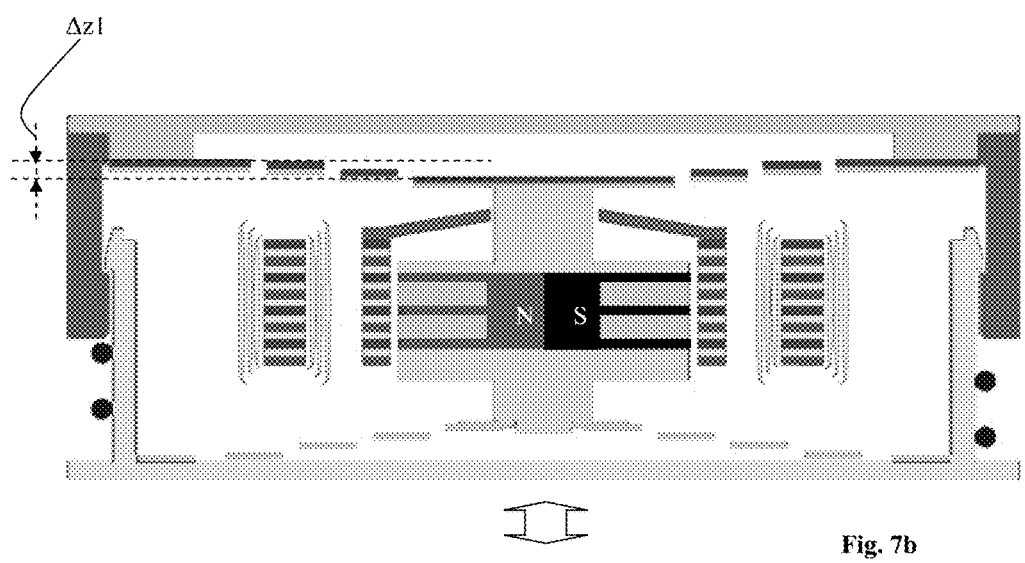

FIGS. 7a and 7b illustrate the dynamic motions mode.

The mechanical solicitation (vibration random or not, shock) is applied on the whole energy harvesting system. The HF mass will act as a seismic mass. A relative displacement $\Delta z1$, between the HF mass and the magnetic circuit, parallel to the z-axis will occur. Two cases can be differentiated:

The acceleration is lower than a threshold value: the HF mass oscillates around one equilibrium position The acceleration is higher than the threshold value: the HF mass snaps from one equilibrium position to another equilibrium position. In this case, the energy conversion is higher.

Figure 8A:
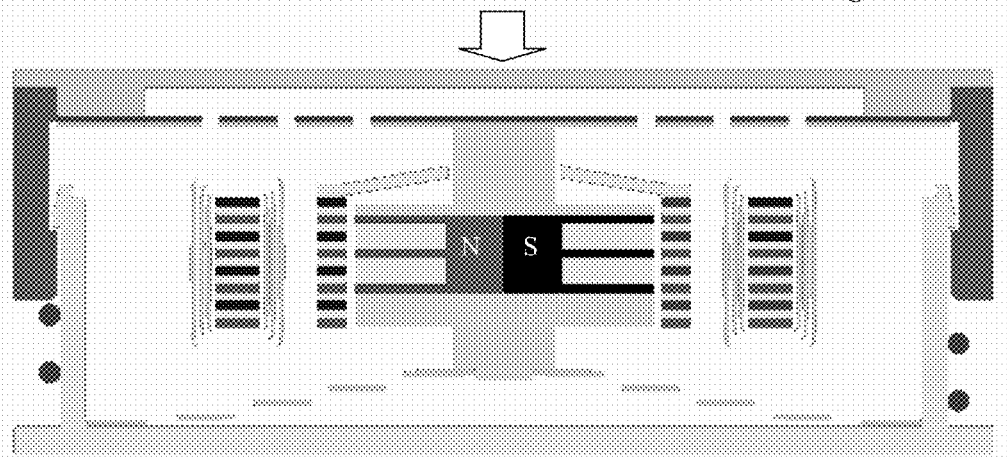
FIGS. 8a and 8b are sectional views illustrating the working of the second of an energy harvesting system according to the invention, for harvesting energy of a slow motion.
Figure 8B:
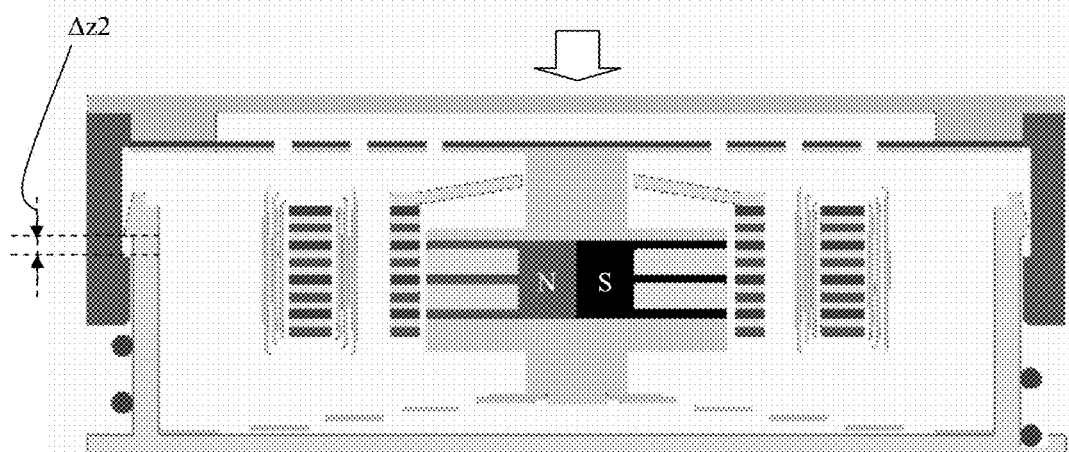

FIGS. 8a and 8b illustrate the slow motions mode.

A slow displacement $\Delta z2$ is applied on the push button, i.e. the hot plate combined with the outer cylinder.

As the movement is low, the load is relayed from the hot plate to the HF mass through the spring/thermoactuator 112, working as a simple spring. The HF mass shifts with the push button along the z-axis.

As long as the displacement is large compared to the step size, many pulses are created during the displacement because of the inversion of magnetic flux. Each pulse corresponds to some electrical energy amount, that can be used by the microsystem directly or at a later time. The speed of the displacement can be very low while keeping a high efficiency for the energy conversion.

Figure 9A:
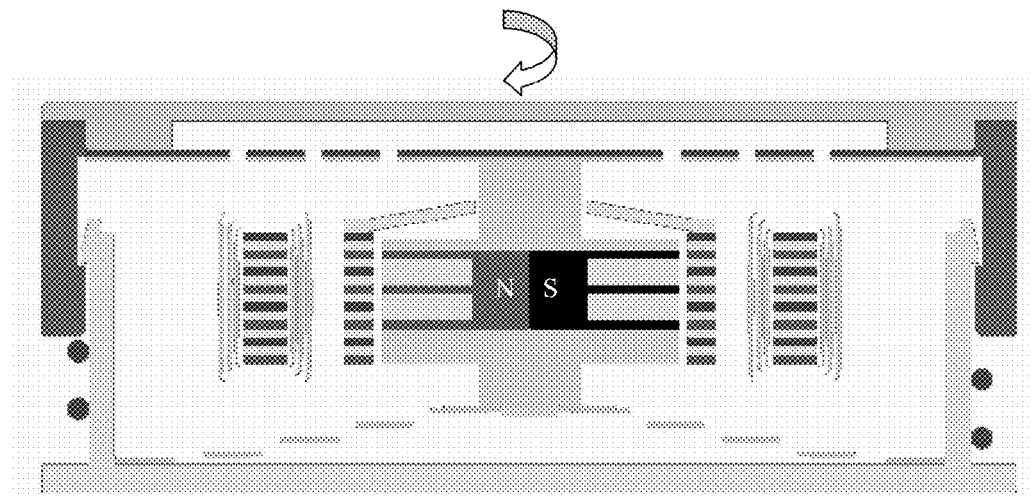
FIGS. 9a and 9b are sectional views illustrating the working of the second of an energy harvesting system according to the invention, for harvesting energy of a rotation.
Figure 9B:
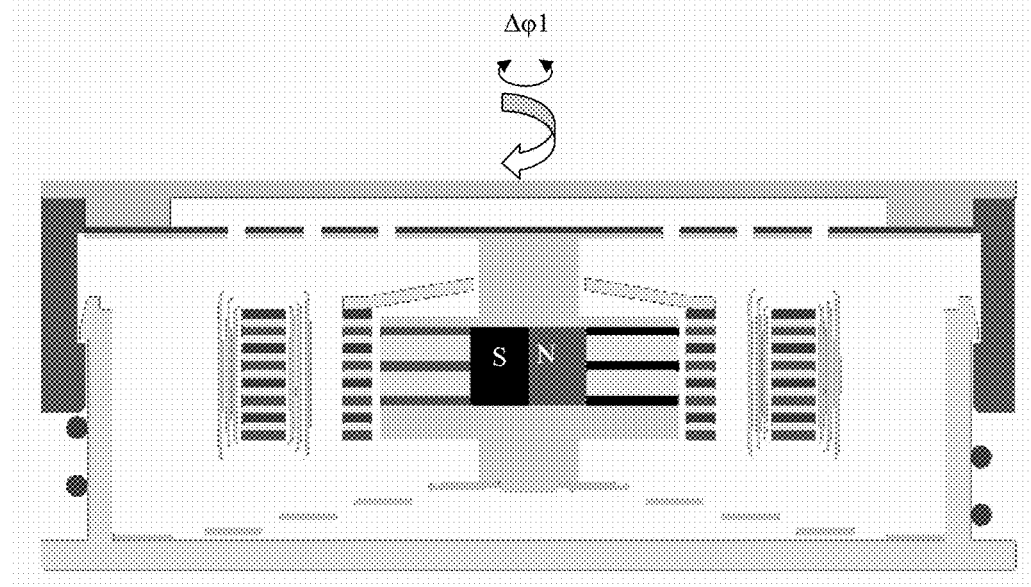

FIGS. 9a and 9b illustrate the rotation mode. A relative rotation $\Delta\phi1$ between cold block 109 and the push button 110 is applied.

In the rotation mode, the rotation is faster than the rotating natural frequency of the spring/thermoactuator 112 due to its moment of inertia. In that case, the twist of the spiral spring 112 remains approximately constant. It follows that the position of the spreaders 114 along the z axis remains unchanged. The inversion of magnetic flux is then only a consequence of the rotation of the permanent magnet 101 around the z axis, as in a conventional electric motor: every half revolution, the direction of the magnetic flux, existing in the magnetic plates located in front of the spreaders, is inverted. A voltage appears at the end of the windings due to Faraday's law.

Figure 10A:
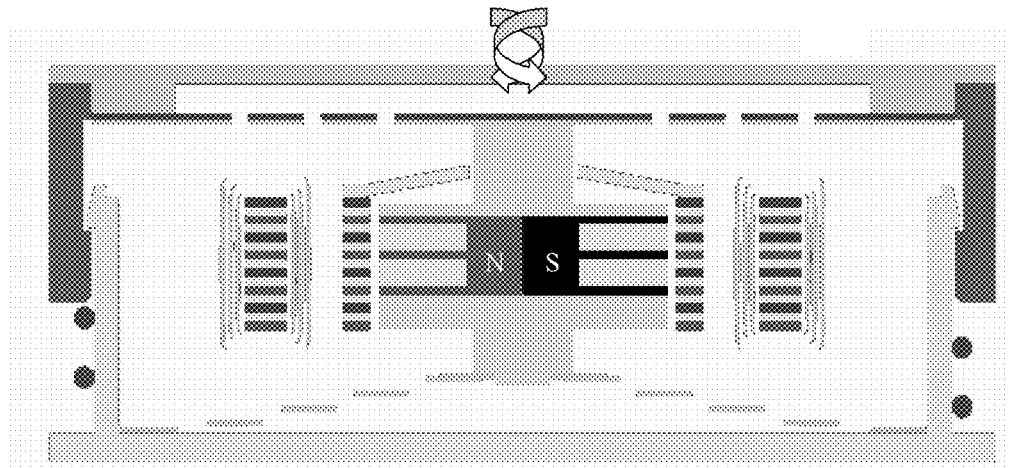
FIGS. 10a and 10b are sectional views illustrating the working of the second of an energy harvesting system according to the invention, for harvesting energy of a small swing.
Figure 10B:
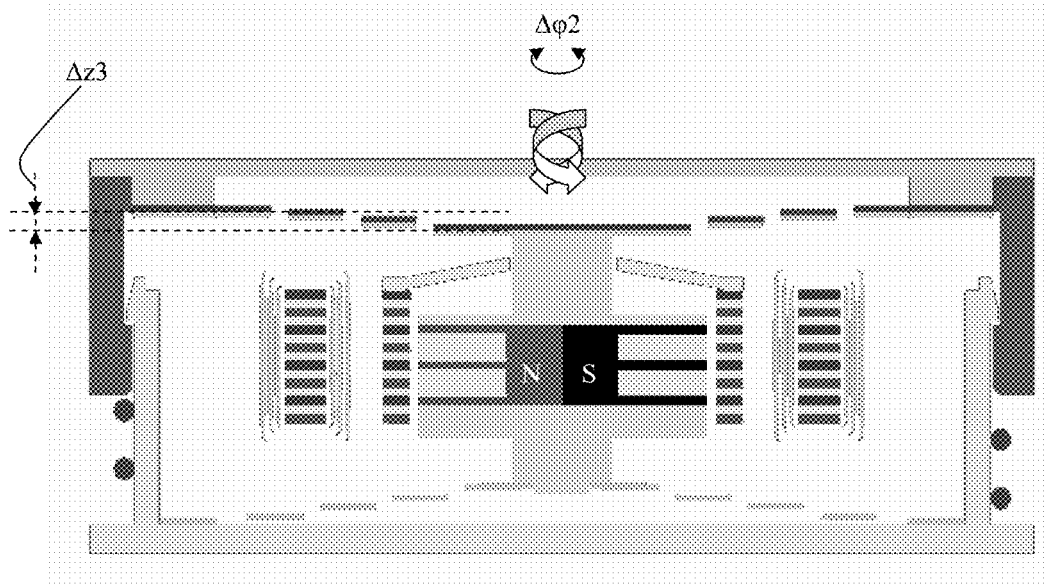

FIGS. 10a and 10b illustrate the small swing mode. Small alternative rotations $\Delta\phi2$ are applied between the cold block 109 and the push button 110.

In the small swing mode, the rotation is slower than the rotating natural frequency of the spring/thermoactuator 112 due to its moment of inertia. The HF mass tends to follow the angle dictated by the hot plate 110. However, as there is a strong interaction between the spreaders 114 and the magnetic circuit 103, it appears variable amplitude torsion in the spiral spring 112. For small angles (smaller than 180°), the torsion is less than the holding torque (magnetic interaction). It follows that the spring/thermoactuator 112 subjected to a torque will cause a small displacement $\Delta z3$ along the z-axis as well as a small swing along the z-axis. The vertical and angular displacements of the spreaders 114 generate a voltage at the end of the windings due to Faraday's law.

As a remarque, in practice it is possible that the rotation mode is accompanied by a vertical displacement if the rotation is not fast enough regarding the rotating natural frequency of the spring/thermoactuator 112 due to its moment of inertia. In this case, the energy is in any case produced by a mix of rotation mode and small swing mode.

Figure 11A:
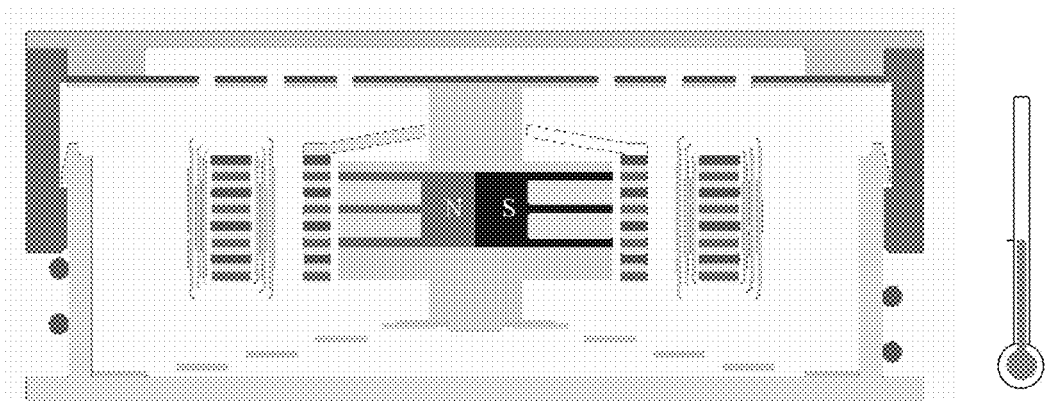
FIGS. 11a and 11b are sectional views illustrating the working of the second of an energy harvesting system according to the invention, for harvesting energy of a slow temperature variation.
Figure 11B:
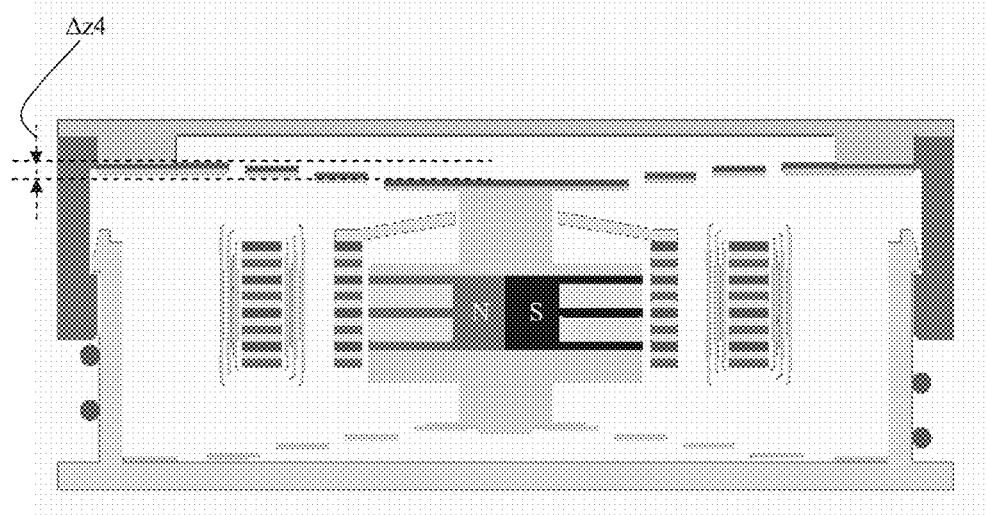

FIGS. 11a and 11b illustrate the slow temperature variation mode. In this case, let consider that the temperature of the whole system is increasing by example. The thermoactuator 112, depicted in FIG. 11a-11b, will be deformed pushing the HF mass to shift downwards along the z-axis. If the deflection $\Delta z4$ is at least larger than the step size, a pulse (or more) is created. So doing, a voltage appears at the end of the windings due to Faraday's law.

Note that the temporary energy storage through a spring system offers to the system to work even if the temperature variation is very slow. The conversion of energy stored will be delayed until the snap between two equilibrium positions.

FIGS. 12a and 12b illustrate the heat flux mode. In this case, let consider that the thermoactuator 112 and the hot plate 110a are initially cold. As soon as the hot plate is heated (e.g. sunrays), the thermoactuator, thermally linked to the hot plate, starts to be deformed. So doing, the HF mass shifts downwards with a deflection $\Delta z5$ and pulses are created. The motion continues until the thermoactuator touches the cold fingers 117. At that time, heat is extracted from the thermoactuator and its temperature decreases. As the thermoactuator is cooling down, the HF mass moves upwards and new pusles are created. The thermoactuator will reach a minimum temperature before to heat again. Then a new cycle start again.

Note that both the period of one cycle and the value of the two extreme temperatures depend of the thermal characteristic time. As the outer cylinder 110b has a low thermal conductivity, the mean thermal resistance of the whole system should be high. Indeed, most of the time, the hot plate is isolated from the cold block. This point makes the system very attractive compared to thermogenerators.

Besides the multisource aspect, the second advantage of the system is that it has been designed in order to reduce losses, leading to a high efficiency.

First of all, the actuation of the spring-mass system is realized through a non contact method based on a magnetic interaction. No mechanical contacts avoid losses and wear-out effect. Moreover, no mechanical interference is possible between the moving parts and fixed parts, and thus no energy losses. A lot of existing systems are based on the opening or the closing of a magnetic path. In the invention, a large amount (around 95%) of energy is harvested after the snap, i.e. during the damped oscillation.

If vacuum surround the HF mass, friction between air and moving parts is drastically reduced. Then the damping of the mechanical oscillation is lowered. The use of a very low loss modulus material to constitute the spring system leads to lower losses. The speed of the mechanical oscillation—by choosing the natural frequency—is kept not too high to reduce friction losses between the moving parts and the remaining air particles. The surface perpendicular to the movement is minimized as well.

The temporarily energy storage using a spring system is very efficient, particularly for long period of storage, because of no auto-discharge effects.

The main idea to lower the electrical losses is to transfer electrical energy at very low currents (involving high voltage). Indeed, currents will induce losses (mainly in the windings) because of Joule effect. Besides that, diodes are generally used in the rectifier circuit, linked to energy losses.

This type of losses is decreased if very low currents and high voltages are used. Moreover, the voltage must exceed the threshold voltage of the diodes. The frequency of the system is also made considering the impedances of the inductances and capacitors used in the harvesting circuit. Indeed, the current amplitude is influenced by the frequency of the induced voltage. In the same way, realizing a low damped oscillation allows one to increase the duration of the energy conversion corresponding to a pulse. The longer the conversion is, the lower the losses are.

Again, the magnetic flux inversion just during the snap between two equilibrium positions brings to a high voltage which improves the efficiency. Increasing the number of turn of the coil and choosing a right frequency, the maximum voltage reached experimentally goes up to 80V.

The skin-effect losses are negligible due to the low value of the natural frequency of the system.

The design of the windings (number of turns, wire diameter, . . . ) results from efficiency aspects.

The magnetic material used in the system according to the invention should consist in a low losses material, e.g. lamination steel. The plates are made by stacking insulated foils. So doing, losses induced by hysteresis or Eddy currents are lowered. The natural frequency of the system must be chosen regarding the previous aspects.

The air gap, in the second embodiment, has to be kept as small as possible to reduce the leakage flux. So doing, the magnetic force, and thus the energy stored in the spring, is enhanced. Moreover, the amplitude peak to peak of the induced voltage occurring during the switch is enlarged.

Heat transfer is involved in mode e and mode f. In mode f, it is important to force the heat flux to pass through the thermalactuator 112. That is why low thermal conductive materials are used for the adiabatic walls or the outer cylinder. If vacuum is realized in the cavity, heat flux leakage are lowered as well. The hot and the cold panels must show a good interface with the heat source(s) (low roughness, black surface, heat sink under the cold panel, etc.).

Contrary to thermogenerators, the system according to the invention, the mode f never works in a thermal equilibrium. The difference temperature between the cold and the hot panel grows during the elastic energy storage. Indeed, no thermal path is established between the hot and the cold panel most of the time.

The miniaturization of the energy harvesting system (second embodiment) allows to increase the number of energy increment for a given displacement ($\Delta z$) or a given temperature variation ($\Delta T$). In the compact version, one can use the caliper principle, combined to the thinning of spreaders to decrease the step existing between two equilibrium positions. As the number of pulse is large, the energy increment can be small. Dividing a large amount of energy into small quantities is beneficial because:
- the efficiency of the energy transfer during the pulse is improved (low power and low current)
- the size of the spring system used for the temporarily storage can be reduced.

For a given size of the energy converter, it can be interesting to use the piezoelectric effect to produce more energy, provided that the addition of a piezoelectric converter does not depreciate the overall efficiency.

Numerous alternatives may be added without exiting from the scope of the invention. Indeed, numerous parameters may be optimized.

Even if the described system is mainly dedicated for energy harvesting to power microsystems, it can be use in various ways:
- As an electrical generator, by increasing the size of the model to enhance the output power
- As an actuator. Focusing only on the 'Slow motions' mode (see description relative to FIGS. 8a-8b), the system can be seen as a reversible machine. It means that if electrical power is feeding the system, a linear motion appears parallel to the z-axis. The linear motion can be controlled step by step in this specific mode. In the same manner, a rotation can be generated focusing on mode c or d.
- As an electrical motor, focusing on mode c. In that case, in order to enhance the output power, the size of the device should be scaled up.

The invention claimed is:

1. An energy harvesting system comprising a frame, at least one permanent magnet having a North/South direction, and at least one winding wound according to a winding direction around a core comprising a high magnetic permeability material, one permanent magnet being mounted on the frame to be able to oscillate relatively to the winding, wherein the system comprises a magnetic flux divider arranged between said at least one permanent magnet and said at least one winding in order to concentrate the magnetic flux at discrete positions of maximum magnetic flux then forming equilibrium positions where the winding faces one of the said discrete positions of maximum magnetic flux, and wherein the magnetic flux divider comprises at least two magnetic guides made of a material having high magnetic permeability, separated by a magnetic and electric isolator made of non conductive and non magnetic material, the magnetic guides being arranged between said at least one permanent magnet and said at least one winding.

2. The energy harvesting system according to claim 1, wherein the magnetic flux divider comprises a stack of a plurality of permanent magnets separated from each other by a fixed spacing, the polarizations North/South of two consecutive magnet being alternated.

3. An energy harvesting system comprising a frame, at least one permanent magnet having a North/South direction, and at least one winding wound according to a winding direction around a core comprising a high magnetic permeability material, one permanent magnet being mounted on the frame to be able to oscillate relatively to the winding through action of an energy converter, wherein the system comprises a magnetic flux divider arranged between said at least one permanent magnet and said at least one winding in order to concentrate the magnetic flux at discrete positions of maximum magnetic flux then forming equilibrium positions where the winding faces one of the said discrete positions of maximum magnetic flux, wherein it comprises:
- a cantilever beam with a clamped extremity to the frame and a free extremity, the beam having a beam core made of a material allowing an oscillating movement of the free extremity;
- a high frequency mass mounted at the free extremity of the cantilever beam, the high frequency mass being formed by the winding wound around a mass core comprising a high magnetic permeability material,
- at least two permanent magnets fixed and arranged to a magnet support made of high magnetic permeability material, such that
    the North/South direction is perpendicular to the magnet support, the permanent magnets are separated from each other by a fixed spacing, that magnet polarizations are alternated, and in that the winding faces the at least two permanent magnets such that the winding direction is parallel to the North/South direction and such that the winding is separated from the permanent magnets by a fixed spacing.

4. The energy harvesting system according to claim 3, wherein the magnet support is elastically mounted relatively to the frame.

5. The energy harvesting system according to claim 3, wherein the beam core is made of a material chosen from a spring material, a shape-memory alloy, and a bimetallic assembly.

6. The energy harvesting system according to claim 3, wherein the beam further comprises an external layer made of piezoelectric material.

7. An energy harvesting system comprising a frame, at least one permanent magnet having a North/South direction, and at least one winding wound according to a winding direction around a core comprising a high magnetic permeability material, one permanent magnet being mounted on the frame to be able to oscillate relatively to the winding through action of an energy converter, wherein the system comprises a magnetic flux divider arranged between said at least one permanent magnet and said at least on winding in order to concentrate the magnetic flux at discrete positions of maximum magnetic flux then forming equilibrium positions where the winding faces one of the said discrete positions of maximum magnetic flux, wherein it comprises, in a rest position:

a permanent magnet elastically mounted on the frame, the permanent magnet further comprising, at each pole, spreaders made of a material having high magnetic permeability, a magnetic circuit comprising magnetic plates alternatively stacked in a stack direction with plates made of non conductive and non magnetic material to electrically and magnetically insulate the magnetic plates from each other, the North/South direction of the magnet being perpendicular to the stack direction, the magnetic circuit facing both the North and South poles of the permanent magnet, at least one winding wound around at least one part (103a) of the magnetic circuit located in a same side as the North Pole of the permanent magnet in a rest position, at least one winding wound around at least one part of the magnetic circuit located in a same side as the South Pole of the permanent magnet in the rest position.

8. The energy harvesting system according to claim 7, wherein the frame is a housing comprising a container and a lid elastically mounted on each other via a spring.

9. The energy harvesting system according to claim 8, wherein the support of the magnetic circuit is fixed on the container and the spring comprising the thermoactuator is fixed to the lid.

10. The energy harvesting system according to claim 7, wherein the magnetic plates have a ring shape part, further comprising two cantilever arms extending along opposite internal directions of the ring shape part, such that, when positioned in the energy harvesting system, the cantilever arms are facing the poles of the permanent magnet, the ring part surrounding the cantilever arms and the magnet.

11. The energy harvesting system according to claim 10, wherein the ring shape is chosen from a rectangular ring shape, a square ring shape, an oval ring shape, and a circular ring shape.

12. The energy harvesting system according to claim 10, wherein the cantilever arms are symmetrical relative to a center of the ring shape.

13. The energy harvesting system according to claim 12, wherein consecutive magnetic plates are arranged such that their respective arms are in same positions.

14. The energy harvesting system. according to claim 12, wherein consecutive magnetic plates are arranged such that their respective arms are in opposite positions.

15. The energy harvesting system according to claim 7, wherein the permanent magnet is elastically mounted on the frame by two opposite springs.

16. The energy harvesting system according to claim 15, wherein at least one of the springs is flat spiral spring comprising at least one spiral blade wider than thicker.

17. The energy harvesting system according to claim 16, wherein one of the springs is a thermoactuor able to move the permanent magnet when the thermoactuor is subjected to a temperature change.

18. The energy harvesting system according to claim 17, wherein the thermoactuator is chosen from a bimetallic element, a shape memory alloy, and an element comprising a phase change material.

19. The energy harvesting system according to claim 17, wherein the magnetic circuit support further comprises thermally conductive fingers arranged relative to the spring comprising the thermoactuator in order to contact and cool the thermoactuator when it is deformed in response to a given temperature change.

20. The energy harvesting system according to claim 7, wherein the permanent magnet and the spreaders are embedded in a holder fixed to the springs.

21. The energy harvesting system according to claim 7, wherein the magnetic circuit is fixed to the frame by the support of the magnetic circuit.

* * * * *